US011086970B2

(12) United States Patent
Jaramaz et al.

(10) Patent No.: US 11,086,970 B2
(45) Date of Patent: Aug. 10, 2021

(54) SYSTEMS AND METHODS FOR USING GENERIC ANATOMY MODELS IN SURGICAL PLANNING

(71) Applicant: Blue Belt Technologies, Inc., Plymouth, MN (US)

(72) Inventors: Branislav Jaramaz, Pittsburgh, PA (US); Constantinos Nikou, Monroeville, PA (US)

(73) Assignee: Blue Belt Technologies, Inc., Plymouth, MN (US)

( * ) Notice: Subject to any disclaimer, the term of this patent is extended or adjusted under 35 U.S.C. 154(b) by 645 days.

(21) Appl. No.: 14/164,883

(22) Filed: Jan. 27, 2014

(65) Prior Publication Data

US 2014/0278322 A1    Sep. 18, 2014

Related U.S. Application Data

(60) Provisional application No. 61/779,805, filed on Mar. 13, 2013.

(51) Int. Cl.
*G06G 7/48* (2006.01)
*C12M 1/00* (2006.01)
*G06F 19/00* (2018.01)
*A61B 34/10* (2016.01)
*G16H 50/50* (2018.01)
*A61B 5/00* (2006.01)
*A61B 17/56* (2006.01)
*A61B 17/17* (2006.01)
*A61B 90/00* (2016.01)

(52) U.S. Cl.
CPC .............. *G06F 19/00* (2013.01); *A61B 34/10* (2016.02); *G16H 50/50* (2018.01); *A61B 5/4504* (2013.01); *A61B 5/4571* (2013.01); *A61B 17/175* (2013.01); *A61B 2017/564* (2013.01); *A61B 2034/101* (2016.02); *A61B 2034/105* (2016.02); *A61B 2090/364* (2016.02)

(58) Field of Classification Search
None
See application file for complete search history.

(56) References Cited

U.S. PATENT DOCUMENTS

| | | |
|---|---|---|
| 5,086,401 A | 2/1992 | Glassman et al. |
| 5,408,409 A | 4/1995 | Glassman et al. |
| 5,571,110 A | 11/1996 | Matsen, III et al. |
| 6,205,411 B1 | 3/2001 | DiGioia, III et al. |
| 6,767,554 B2 | 7/2004 | Porta et al. |
| 8,126,533 B2 | 2/2012 | Lavallee et al. |
| 9,173,716 B2 | 11/2015 | Kasodekar et al. |
| 9,585,725 B2 | 3/2017 | Bonutti |
| 2003/0153978 A1 | 8/2003 | Whiteside |
| 2011/0130761 A1* | 6/2011 | Plaskos .................. A61B 34/30 606/87 |
| 2013/0114866 A1* | 5/2013 | Kasodekar ............... G06T 7/13 382/128 |
| 2013/0166256 A1* | 6/2013 | Wirx-Speetjens ...... G06F 30/00 703/1 |

FOREIGN PATENT DOCUMENTS

| | | | |
|---|---|---|---|
| JP | 2001502565 | A | 2/2001 |
| JP | 2003530177 | A | 10/2003 |
| JP | 2008531163 | A | 8/2008 |
| WO | 9814128 | A1 | 4/1998 |
| WO | 1998014128 | | 4/1998 |
| WO | 2001078015 | A2 | 10/2001 |
| WO | WO-01/78015 | A2 | 10/2001 |
| WO | 2006092600 | | 9/2006 |
| WO | 2006092600 | A1 | 9/2006 |
| WO | 2011158115 | A2 | 12/2011 |
| WO | WO-2011/158115 | A2 | 12/2011 |
| WO | 2012014036 | A2 | 2/2012 |

(Continued)

OTHER PUBLICATIONS

"Mathematical representation of the normal proximal human femur: Application in planning of cam hip surgery," Masjedi et al., Proc IMechE Part, H: J. Engineering in Medicine, Published online Nov. 19, 2012, pp. 1-7 [online]<http://pih.sagepub.com/content/early/2012/11/16/0954411912466353.full.pdf+html>.*
Barrett et al. "Computer-assisted hip resurfacing surgery using the AcrobotA Navigation System," Proc. IMechE vol. 221 Part H: J. Engineering in Medicine, vol. 221 (2007) pp. 773-783.*
"International Application Serial No. PCT/US2014/021888, International Search Report dated Jun. 26, 2014", 5 pgs.
"International Application Serial No. PCT/US2014/021888, Written Opinion dated Jun. 26, 2014", 8 pgs.
"Msk Lab—Planning Femoro-Acetabular Impingement Surgery", [online]. (c) 2012 Imperial College London [retrieved on Jun. 13, 2014]. Retrieved from the Internet: <URL: http://www1.imperial.ac.uk/msklab/research/surgicaltechniques/femero_acetabularimpingementsurgery/>, (2012), 2 pgs.

(Continued)

*Primary Examiner* — Anna Skibinsky
(74) *Attorney, Agent, or Firm* — Troutman Pepper Hamilton Sanders LLP

(57) ABSTRACT

Systems and methods for generating a surgical plan for altering an abnormal bone using a generic normal bone model are discussed. For example, a system for planning a surgery on an abnormal bone can include a model receiver module configured to receive a generic normal bone model. The generic normal bone model, such as a parametric model derived from statistical shape data, can include a data set representing a normal bone having an anatomical origin comparable to the abnormal bone. An input interface can be configured to receive an abnormal bone representation including a data set representing the abnormal bone. A surgical planning module can include a registration module configured to register the generic normal bone model to the abnormal bone representation by creating a registered generic model. A surgical plan formation module can be configured to identify one or more abnormal regions of the abnormal bone using the registered generic model.

21 Claims, 6 Drawing Sheets

(56) References Cited

FOREIGN PATENT DOCUMENTS

| WO | 2012014036 A3 | 2/2012 |
| WO | 2011158115 A3 | 11/2012 |
| WO | 2014159082 A1 | 10/2014 |
| WO | WO-2014/159082 A1 | 10/2014 |

OTHER PUBLICATIONS

"Smith & Nephew Digital Communications: DYONICS* Plan Hip Impingement Planning System", [online], [retrieved on Jun. 13, 2014]. Retrieved from the Internet: <URL: https://www.youtube.com/watch?v=7EJM1j37tEU>, (Jan. 14, 2014), 1 pg.

Krekel, Peter, "Hip Impingement Detection", [online]. [retrieved on Jun. 13, 2014]. Retrieved from the Internet: <URL: https://www.youtube.com/watch?v=fWfoMOy4BoA>, (May 1, 2009), 1 pg.

Japanese Office Action dated Nov. 7, 2016.

Translation of Japanese Office Action.

Chao et al. "Simulation and Animation of Musculosketal Joint System" (Nov. 1, 1993) J. Biomechanical Engineering 115(4B): 562-568.

International Search Report and Written Opinion for PCT/US2014/02188 dated Jun. 26, 2014.

Troccaz et al. "The Use of Localizers, Robots and Synergistic Devices in CAS" (Nov. 21, 2005) First Joint Conference: Computer Vision, Virtual Reality and Robotics in Medical and Medical Robotics and Computer-Assisted Surgery 1205: 725-736.

Delp et al. "An Interactive Graphics-Based Model of the Lower Extremity to Study Orthopaedic Surgical Procedures" (Aug. 1990) IEE Transactions on Biomedical Engineering 37(8): 757-767.

DiGioia et al. "An Integrated Approach to Medical Robotics and Computer Assisted Surgery in Orthopaedics" (1995) Carnegie Mellon University 106-111.

DiGioia et al. "HipNav: Pre-operative Planning and Intra-operative Navigational Guidance for Acetabular Implant Placement in Total Hip Replacement Surgery" (Nov. 1995) Preceedings of CAOS '96 1-8.

Harris et al. "Experiences with Robotic Systems for Knee Surgery" (Mar. 19-22, 1997) Springer-Verlag, London, UK 757-766.

Freysinger et al. "A Passive-Marker-Based Optical System for Computer-Aided Surgery in Otorhinolaryngology: Development and First Clinical Experiences" (Feb. 2002) The Laryngoscope 112(2):409.

O'Toole III et al. "Towards More Capable and Less Invasive Robotic Surgery in Orthopaedics" (1995) Computer Vision, Virtual Reality and Robotics in Medicine 905: 123-130.

Taylor et al. "An Image-Directed Robotic System for Precise Orthopaedic Surgery" (Jun. 1994) IEE Transactions on Robotics and Automation 10 (3): 261-275.

Straka et al. "Bone segmentation in CT-angiography data using a probabilistic atlas." VMV. 2003.

"Smith & Nephew Digital Communications : Dyonics* Plan Hip Imingement Planning System" (Jan. 14, 2014) retrieved from the internet: URL: https://www.youtube.com/watch?v=7EJM1j37tEU.

"MSK Lab-Planning Femoro-Acetabular Impingement Surgery" (2012) Imperial College London, Retrieved from the Internet: URL:http://www1.imperial.ac.uk/msklab/research/surgicaltechniques/femero_acetabluarimpingementsurgery/.

Dillman et al. "Haptic Devices in Medical Applications" (Jun. 23, 1999) Institute for Process Control and Robotics, 1st International Workshop, Paris, France, pp. 12-22.

Krekel, Peter "Hip Impingement Detection". May 1, 2009, XP054975420, Retrieved from the internet: URL: https://www.youtube.com/watch?v=fWfoMOy4BoA.

Japanese Office Action for JP20160500873 dated Nov. 7, 2016.

Bryan et al. "Statistical Modelling of the Whole Human Femur Incorporating Geometric and Material Properties" 2010, Medical Engineering and Physics 32:57-65.

European Office Action for EP 14716474.3 dated Apr. 24, 2018.

European Office Action for EP 14716474.3 dated Oct. 11, 2019.

European Office Action for EP 14716474.3 dated Mar. 28, 2017.

* cited by examiner

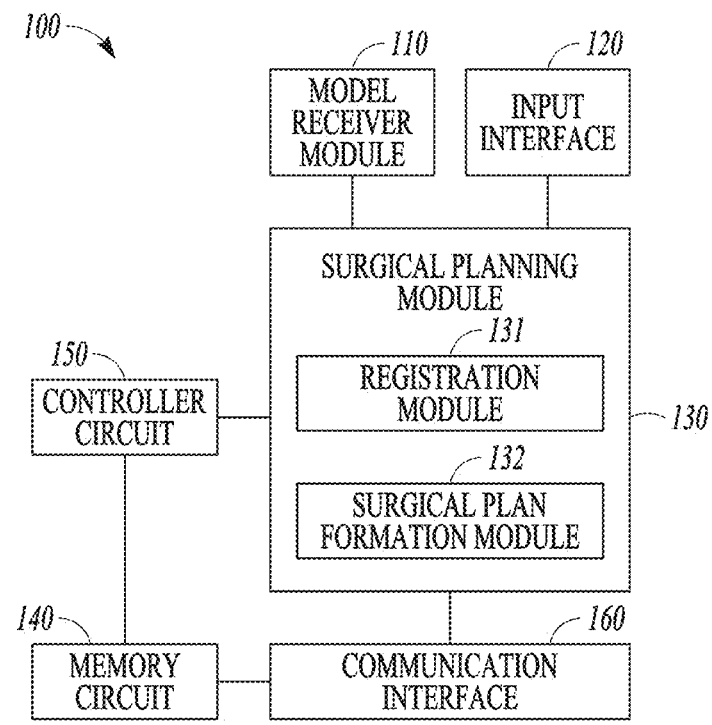
FIG. 1
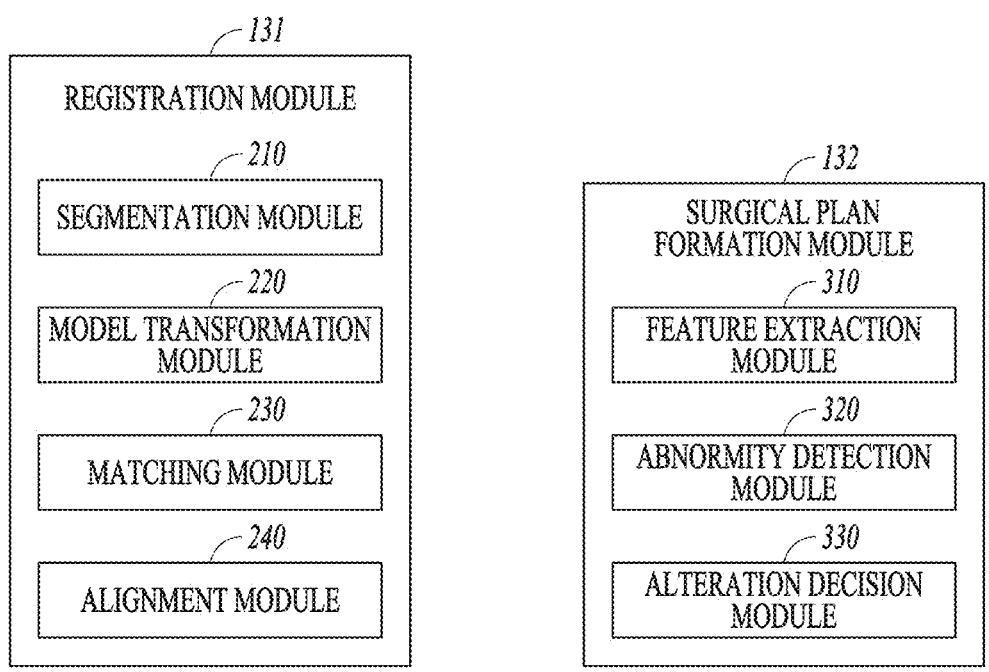
FIG. 2
FIG. 3

SYSTEMS AND METHODS FOR USING GENERIC ANATOMY MODELS IN SURGICAL PLANNING

RELATED APPLICATIONS

This patent application claims the benefit of priority to U.S. Provisional Patent Application Ser. No. 61/779,805, filed on Mar. 13, 2013, which is hereby incorporated by reference herein in its entirety.

TECHNICAL FIELD

This document relates generally to computer-aided orthopedic surgery, and more specifically to systems and methods for generating surgical plan for altering an abnormal bone using generic normal bone models.

BACKGROUND

The use of computers, robotics, and imaging to aid orthopedic surgery is well known in the art. There has been a great deal of study and development of computer-aided navigation and robotics systems used to guide surgical procedures. For example, a precision freehand sculptor (PFS) employs a robotic surgery system to assist the surgeon in accurately cutting the prosthesis into a desired shape. In interventions such as total hip replacement, computer-aided surgery techniques have been used to improve the accuracy, reliability of the surgery. Orthopedic surgery guided by images has also been found useful in preplanning and guiding the correct anatomical position of displaced bone fragments in fractures, allowing a good fixation by osteosynthesis.

Femoral acetabular impingement (FAI) is a condition characterized by abnormal contact between the proximal femur and rim of the acetabulum. In particular, impingement occurs when the femoral head or neck rubs abnormally or does not have full range of motion in the acetabular socket. It is increasingly suspected that FAI is one of the major causes of hip osteoarthritis. Cam impingement (CI) and pincer impingement are two major classes of FAI. CI results from pathologic contact between an abnormally shaped femoral head and neck with a morphologically normal acetabulum. The femoral neck is malformed such that the hip range of motion is restricted and the deformity on the neck causes the femur an acetabular rim to impinge on each other. This can result in irritation of the impinging tissues and is suspected as one of the main mechanisms for development of hip osteoarthritis. Pincer impingement is the result of contact between an abnormal acetabular rim and a typically normal femoral head-neck junction. This pathologic contact is the result of abnormal excess of growth of anterior acetabular cup. This results in decreased joint clearance and repetitive contact between the femoral neck and acetabulum, leading to degeneration of the anterosuperior labrum.

SUMMARY

Arthroscopic or open surgery interventions have been developed for treating FAI. The goal of surgical intervention is to relieve the impingement by increasing hip clearance in flexion or some other motions as well as addressing the associated labral and chondral pathology. Surgical treatment of CI, for example, includes removal of the excess bone from the femoral neck, to recreate the anatomic sphericity of the femoral head and to reduce the prominence of the femoral neck which abuts the anterior labrum and acetabulum. The excess bone on the proximal femur can be removed by a surgeon using surgical tools such as a high speed bur or an arthroscopic shaver.

To plan for the surgical repair of the target pathological bone, the deformity of the bone, such as the prominent femoral head-neck region in CI, needs to be identified and defined. Deformity can be identified on output from a magnetic resonance (MR) arthrogram or a computed tomography (CT) scan. In many cases, a surgeon is required to mentally map the deformity area to the operative bone. Computer-aided tools can be used in more advanced procedures to define the bone removal volume, either by looking at the simulated hip motion and the resulting zones of impingement, or by fitting an idealized axisymmetric surface to the femoral neck. These methods, however, can be difficult to operate and may suffer from lack of reliability and certainty. For example, the impingement area can have reduced visualization and access, particularly during minimally invasive surgery and arthroscopic techniques. Identifying the impingement zones can be problematic due to, for example, the flexion of the hip joint and the interference of surrounding soft tissues. Determining and visualizing the correct amount of bone that should be removed can be practically difficult, without removing too much bone. Therefore, the present inventors have recognized that there remains a considerable need for systems and methods that can efficiently and reliably identify the abnormity of a pathological bone, determining the shape and volume of the bone to be removed, and generating a surgical plan accordingly, which can be used within a robotic surgical cutting instrument to perform the planned procedure.

Various embodiments described herein can help improve the efficacy and the reliability in osteoplasty planning. For example, a system for planning a surgery on an abnormal bone can include a model receiver module that is configured to receive a generic normal bone model. The generic normal bone model, such as a statistical shape model, can include a data set representing a normal bone having an anatomical origin comparable to the abnormal bone. An input interface can be configured to receive an abnormal bone representation including a data set representing the abnormal bone. A surgical planning module can include a registration module configured to register the generic normal bone model to the abnormal bone representation by creating a registered generic model. A surgical plan formation module can be configured to identify one or more abnormal regions of the abnormal bone using the registered generic model.

A machine-readable storage medium embodiment can include instructions that, when executed by a machine, cause the machine to receive an abnormal bone representation and a generic normal bone model. The abnormal bone representation can include a data set representing an abnormal bone, while the generic normal bone model includes a data set representing a normal bone having an anatomical origin comparable to the abnormal bone. The machine can be caused to register the generic normal bone model to the abnormal bone representation to create a registered generic model. One or more abnormal regions of the abnormal bone can be identified using a comparison between the registered generic model and the abnormal bone representation. The instructions can then cause the machine to generate a surgical plan for altering a portion of the abnormal bone from the one or more abnormal regions.

A method embodiment for planning a surgery on an abnormal bone can comprise the operations of receiving an abnormal bone representation and a generic normal bone model. The abnormal bone representation can include a data set representing the abnormal bone, such as a medical image of the diseased femur. The normal bone model can include a generic normal bone model, such as a statistical shape model of a normal femur derived from a plurality of medical images of normal femurs from a group of subjects. The generic normal bone model can be registered to the abnormal bone representation. One or more abnormal regions of the abnormal bone can be detected using a comparison between the registered generic model and the abnormal bone representation. A surgical plan can then be generated for altering a portion of the abnormal bone from the one or more abnormal regions.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 1 is a block diagram that illustrates an example of a system for planning a surgery on an abnormal bone.

FIG. 2 is a block diagram that illustrates an example of a registration module in a surgery planning system.

FIG. 3 illustrates an embodiment of the surgical plan formation module in a sugary planning system.

DETAILED DESCRIPTION

Figure 4A:
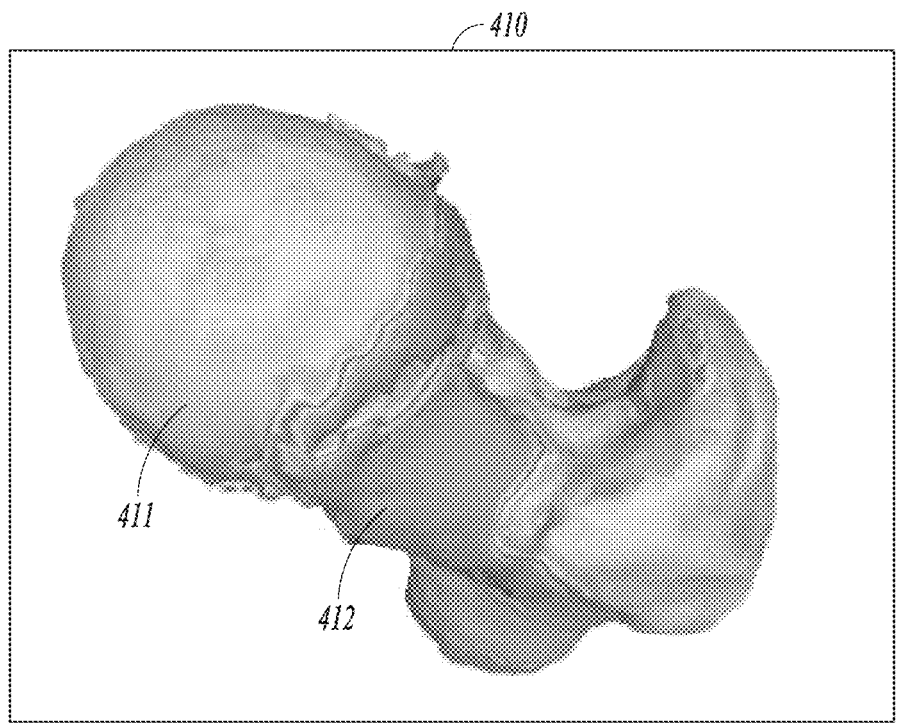
FIGS. 4A-E illustrate examples of deformity of a pathological femur detected using a generic normal femur model.

Disclosed herein are systems, devices and methods for generating a surgical plan for altering an abnormal bone using generic normal bone models. Various embodiments described herein can help improve the efficacy and the reliability in osteoplasty planning, such as removal of excess bone from the femoral neck in cam impingement. The methods and devices described herein can also be applicable to planning surgery of pathological bones under various other conditions.

FIG. 1 is a block diagram that illustrates an example of a system 100 for planning a surgery on an abnormal bone. The system 100 can include a model receiver module 110, an input interface 120, and a surgical planning module 130. The system 100 can also include a memory circuit 140 and a controller circuit 150. Optionally, the system 100 can include a communication interface 160. In an example, the system 100 can generate instructions for operating a surgical tool (such as a surgical navigation system or medical robotics) to alter the abnormal bone, such as by surgically removing an excess portion from the abnormal bone.

The model receiver module 110 can be configured to receive a generic normal bone model. Examples of the normal bone can include a femur, an acetabulum, or any other bone in a body. The generic normal bone model can include a data set representing a normal bone which has an anatomical origin comparable to the abnormal bone to be altered by the system 100. In some examples, the generic normal bone model can represent the shape or appearance of the anatomical structure of the normal bone. The generic normal bone model can be in a form of a parametric model, a statistical model, a shape-based model, or a volumetric model. The generic normal bone model can also be based on physical properties of the normal bone, such as an elastic model, a geometric spine model, or a finite element model. In a particular example, the generic normal bone model may include a statistical shape (SS) model derived from a plurality of images of normal bones of comparable anatomical origin from a group of subjects known to have normal bone anatomy. The SS model comprises a statistical representation of the normal bone anatomy from the group of subjects. In some examples, the generic normal bone model can represent a desired postoperative shape or appearance of the normal bone. The desired postoperative shape or appearance of the normal bone can be obtained by modifying a normal bone model (such as a parametric model, a statistical model, a shape-based model, or a volumetric model) using a computer software configured for three-dimensional manipulation of the normal bone model.

In some embodiments, the generic normal bone model can be generated using a system external to the system 100, and the generic normal bone model can be stored in a machine-readable medium such as a memory device. The model receiver module 110 can retrieve from the memory device a generic normal bone model that represents an anatomical origin comparable to that of the abnormal bone. In some embodiments, the system 100 can include a generic normal bone model generator configured to be coupled to the model receiver module 110. The normal bone model generator can create a generic normal bone model such as by using shape data or appearance data. The shape data may include geometric characteristics of a bone such as landmarks, surfaces, boundaries of three-dimensional images objections. The appearance data may include both geometric characteristics and intensity information of a bone.

In an example, the shape data or appearance data can be constructed from a plurality of medical images of the normal bones of comparable anatomical origin from a group of subjects. The medical images can include two-dimensional (2D) or three-dimensional (3D) images. Examples of the medical images include an X-ray, an ultrasound image, a computed tomography (CT) scan, a magnetic resonance (MR) image, a positron emission tomography (PET) image, a single-photon emission computed tomography (SPECT) image, or an arthrogram. In another example, the shape data or appearance data can be constructed from a plurality of point clouds acquired from normal bones of comparable anatomical origin from a group of subjects using a coordinated measuring system (such as one or more tracking probes).

In an embodiment, the shape data or appearance data can be constructed from medical images or point clouds of normal bones from a group of subjects with comparable age, gender, ethnicity, size, or other physical or demographical data. For example, the shape data or appearance data may include medical images or point clouds of normal bones from the subjects whose physical or demographical data are comparable to the host (patient) of the abnormal bone being analyzed by the system 100. This would allow the generic normal bone model to specifically represent the abnormal bone under analysis.

The input interface 120 can be configured to receive an abnormal bone representation including a data set representing the shape, appearance, or other morphological characteristics of the abnormal bone. The abnormal bone representation can be analyzed by the system 100 to identify a region of abnormality. The input interface 120 can receive the abnormal bone representation from a patient database. The abnormal bone representation can include one of more of a medical image, a point cloud, a parametric model, or other morphological description of the abnormal bone. In some examples, the input interface 120 can be configured to be coupled to an imaging system or other image acquisition module within or external to the system 100. The imagining system or the image acquisition module can feed the abnormal bone representation (e.g., one or more images or point clouds) to the system 100 via the input interface 120. In some embodiments, the generic normal bone model received from the model receiver module 110 has data format or modality comparable to the abnormal bone representation received from the input interface 120. For example, if the input interface 120 receives a CT scan image of the pathological femur from a patient, then the model receiver module 110 can be configured to receive an SS model derived from CT scans of normal femurs of comparable anatomical origin from a group of patients. In another example, the input interface 120 can receive a CT scan image of the pathological acetabulum from a patient, and the model receiver module 110 can be configured to receive an SS model derived from CT scans of normal acetabula of comparable anatomical origin from a group of patients.

The surgical planning module 130 can be configured to generate a surgical plan for altering a portion of the abnormal bone. As illustrated in FIG. 1, the surgical planning module can include a registration module 131 and a surgical plan formation module 132. The registration module 131 can be configured to register the generic normal bone model to the abnormal bone representation. Due to the anatomical variations across subjects, and/or the extrinsic differences resulted from different data acquisition processes (e.g., the imaging system or the image acquisition processes), the generic normal bone model and the abnormal bone representation may have structural discrepancies resulting in reduced correspondence. The registration module 131 can transform the generic normal bone model into a registered generic model specific to the abnormal bone under analysis. The registered generic model can be in a coordinate system similar to that of the abnormal bone representation. Examples of the registration module 131 are discussed below, such as with reference of FIG. 2.

The surgical plan formation module 132 can be configured to identify one or more abnormal regions of the abnormal bone using comparison of the registered generic model and the abnormal bone representation. In an example, the surgical plan formation module 132 can calculate a level of disconformity between the registered generic model and the abnormal bone representation. The disconformity can be used as a basis for surgical planning Examples of the surgical plan formation module 132 are discussed below, such as with reference of FIG. 3.

The memory circuit 140 can be configured to store the generic normal bone model such as received from the model receiver module 110, the abnormal bone representation such as received from the input interface 120, and a set of instructions controlling operation of individual modules of the system 100 and inter-module data communication. In an example, the registered generic model created by the registration module 131 can be stored in the memory circuit 140.

The controller circuit 150 can be coupled to the surgical planning module 130 and the memory circuit 140. The controller circuit is configured to execute the set of instructions to cause the surgical planning module 130 to generate the surgical plan for altering the portion of the abnormal bone from the one or more abnormal regions.

The communication interface 160, coupled to the surgical planning module 130 and the memory circuit 140, can be configured to generate a representation illustrating one or more of the generic normal bone model, the registered generic model, the abnormal bone representation, and the surgical plan. The communication interface 160 can include a display device configured to present the information in audio, visual, or other multi-media formats to assist the surgeon during the process of creating and evaluating a surgical plan. Examples of the presentation formats include sound, dialog, text, or 2D or 3D graphs. The presentation may also include visual animations such as real-time 3D representations of the generic normal bone model, the abnormal bone representation, the registered generic model, and the surgical plan, among other things. In certain examples, the visual animations are color-coded to further assist the surgeon to visualize the one or more regions on the abnormal bone that needs to be altered according to the surgical plan. In various examples, the communication interface 160 can also include a user input device configured to receive user input to accept or modify the surgical plan generated by the surgical planning module 130.

The communication interface 160 can communicate over an internal bus to other modules within the system 100. In some examples, the communication interface 160 can be configured to communicate with one or more external devices including, for example, a tracking device, a positioning device, a surgical navigation system, or a medical robotic system. The communication interface 160 can include both wired interface (such as cables coupled to the communication ports on the communication interface 160) and wireless connections such as Ethernet, IEEE 802.11 wireless, or Bluetooth, among others.

FIG. 2 is a block diagram that illustrates an example of a registration module 131. The registration module 131 can include a segmentation module 210, a model transformation module 220, a matching module 230, and an alignment module 240. As illustrated in FIG. 1, the registration module 131 can take as input the generic normal bone model and the abnormal bone representation, and generate registered generic model and the alignment between the registered generic model and the abnormal bone representation.

The segmentation module 210 can be configured to partition the generic normal bone model into a plurality of segments. For example, when the generic normal bone model constitutes a medical image or point cloud, the segmentation module 210 can partition the image or the point cloud into segments representing various anatomical structures. In some examples, the segmentation module 210 can be configured to assign a label to each of the segments, such that the segments with the same label share specified characteristics such as a shape, anatomical structure, or intensity. The segmentation module 210 can also partition the abnormal bone representation into a plurality of segments. For example, the segmentation module can differentiate the pathological portion from the normal portion on the abnormal bone representation, and identify from the segments of the abnormal bone representation a registration area free of anatomical abnormity. In some embodiments, the segmentation module 210 can be optional. For example, the segmentation module 210 can be excluded from the registration module 131 when both the generic normal bone model and the abnormal bone representation, when received by the system 100, are segmented images with labels assigned according to the respective anatomical structures.

The model transformation module 220 can transform the generic normal bone model to create a registered generic model such as using a comparison between the area on the abnormal bone free of anatomical abnormity and the corresponding segments of the generic normal bone model. The transformation can include linear or nonlinear operations such as scaling, rotation, translation, expansion, dilation, or other affine transformation. The transformation can include rigid transformations that preserve the distance (such as translation, rotation, and reflection) or non-rigid transformations such as stretching, shrinking, or model-based transformations such as radial basis functions, splines, or finite element model. In some embodiments, the model transformation module 220 can employ both the rigid transformation to bring the generic normal bone model in global alignment with the size and orientation of the abnormal bone representation, and the non-rigid transformation to reduce the local geometric discrepancies by aligning the generic normal bone model with the abnormal bone representation. In some embodiments, the model transformation module 220 can determine a desired transformation $\Theta$ that minimizes the difference between the identified abnormity-free segments on the abnormal bone representation $S_{abnormal}(x,y,z)$ and the corresponding segments of the generic normal bone model $S_{model}(x,y,z)$ generic normal bone model following the transformation $\Theta$. That is, the desired transformation $\Theta_{opt}$ is selected such that the Euclidian distance $\|\Theta_{opt}(S_{model}(x,y,z))-S_{abnormal}(x,y,z)\|$ is minimized. The model transformation module 220 can then apply the desired transformation $\Theta_{opt}$ to the generic normal bone model to create the registered generic model $\Theta_{opt}(S_{model})$.

The matching module 230 can match the registered generic model to the abnormal bone representation. In an embodiment, the matching module 230 can match, in response to identifying the registration area of the abnormal bone, one or more segments of the registered generic model to the corresponding registration area of the abnormal bone. The alignment module 240 can be configured to align the remaining segments of the registered generic model with the remaining segments of the abnormal bone representation based at least in part on the matching.

FIG. 3 illustrates an embodiment of the surgical plan formation module 132. The surgical plan formation module 132 is configured to identify the one or more abnormal regions of the abnormal bone and generate a surgical plan for altering the identified abnormal regions. The surgical plan formation module 132 comprises a feature extraction module 310, an abnormality detection module 320, and an alteration decision module 330.

The feature extraction module 310 is configured to extract a plurality of model features from the registered generic model and a plurality of abnormal bone features from the abnormal bone representation. In an example, types of the extracted features can include one or more geometric parameters such as a location, an orientation, a curvature, a contour, a shape, an area, a volume, or other volumetric parameters. In another example, the extracted features can include one or more intensity-based parameters. The features can be extracted in the space domain, frequency domain, or space-frequency domain. In various examples, the features may include statistical measurements derived from the geometric or intensity-based parameters, such as the mean, median, mode, variance, covariance, and other second or higher order statistics.

The abnormity detection module 320 is configured to identify one or more abnormal regions of the abnormal bone using a comparison between the model features and the abnormal bone features. The comparison can be performed on all or selected segments from the registered generic model and from the abnormal bone representation. In an embodiment, the comparison can be performed only after the registration module 131 matches the segment of the registered generic model to the registration area of the abnormal bone.

The abnormality detection module 320 can detect an abnormal region from a segment of the abnormal bone if a similarity measure between the abnormal bone feature of the segment ($R_{abnormal}(k)$) and the model feature of the corresponding segment on the registered generic model ($R_{model}(k)$) meets a specified criterion. For example, an abnormal region can be detected if the volumetric difference between $R_{abnormal}(k)$ and $R_{model}(k)$ exceeds a specified threshold. In various examples, the abnormity detection module 320 can employ different similarity measures according to the type of the features. The abnormity detection module 320 can also select similarity measure according to the data format (such as the imaging modality or image type) of the abnormal bone representation and the generic normal bone model. For example, if the extracted features from 310 are geometric features, the abnormity detection module 320 can calculate sum of squared distance between the model features and the abnormal bone features, where the distance can be computed as one of L1 norm, L2 norm (Euclidian distance), infinite norm, or other norm in the normed vector space. In another example, if the extracted features are intensity-based features, then the abnormity detection module 320 can calculate the similarity between the model features and the abnormal bone features using one of the measures such as correlation coefficient, mutual information, or ratio image uniformity.

The alteration decision module 330 can be configured to subtract, for the detected abnormal regions, a volumetric parameter ($X_{model}(k)$) of the segment of the registered generic model from a volumetric parameter ($X_{abnormal}(k)$) of the segment of the abnormal bone. The volumetric parameters $X_{model}(k)$ and $X_{abnormal}(k)$ each represents a shape or a volume of the corresponding bone representation. The subtracted volumetric parameter in each of the one or more abnormal regions can be determined as the part of alteration. In some embodiments, the subtraction can be performed between a model feature $R_{model}(k)$ and an abnormal bone feature $R_{abnormal}(k)$. For example, both $R_{model}(k)$ and $R_{abnormal}(k)$ may not represent direct measurement of shape or volume of the corresponding bone representation; rather, $R_{model}(k)$ may be a model feature indirectly representing the volume via a mapping $\Phi$ of a volumetric parameter $X_{model}(k)$ (i.e., $R_{model}(k)=\Phi(X_{model}(k))$), and the abnormal bone feature $R_{abnormal}(k)$ indirectly represents the volume via a mapping $\Phi$ of a volumetric parameter $X_{abnormal}(k)$ (i.e., $R_{abnormal}(k)=\Phi(X_{abnormal}(k))$). The volumetric difference, as part of surgical plan, can be determined by applying the inverse map $\Phi^{-1}$ to the respective features, i.e., $\Phi^{-1}(R_{abnormal}(k))-\Phi^{-1}(R_{model}(k))$.

In an example, the alteration decision module 330 can include instructions for performing a first simulation of the abnormal bone (such as a diseased femur, a diseased acetabulum, or other diseased bones in the body), and a second simulation of the surgically altered abnormal bone such as a simulated model of the post-operative abnormal bone with the identified excess bone tissue removed. One or both of the first and the second simulations can each include a biomechanical simulation for evaluating one or more biomechanical parameters including, for example, range of motion of the respective bone. The alteration decision module 330 can determine the one or more abnormal regions of the abnormal bone using a comparison between the first simulation and the second simulation. In some examples, the alteration decision module 330 can include instructions for incrementally altering the one or more abnormal regions of the abnormal bone by gradually removing the identified excess bone tissue from the abnormal bone such as following a pre-specified procedure.

Figure 4B:
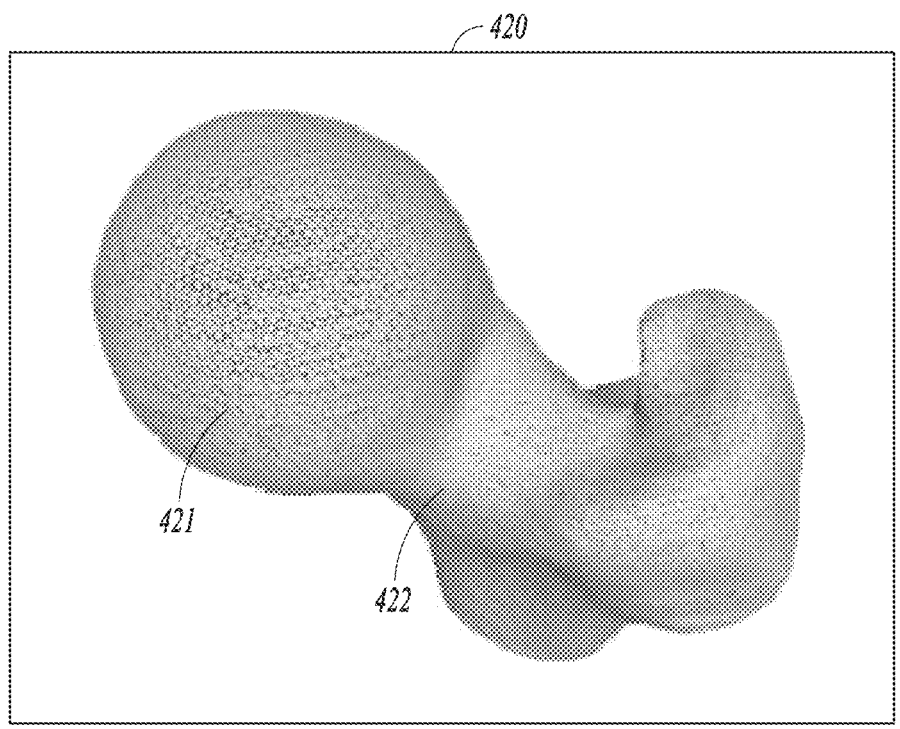

FIGS. 4A-E illustrate examples of deformity of a pathological femur detected using a generic normal femur model. FIGS. 4A-B illustrate an example of a three-dimensional (3D) pathological proximal femur image 410 (as shown in FIG. 4A) with deformed region detected using a 3D generic normal proximal femur model 420 (as shown in FIG. 4B), which can be generated and presented using the system 100 or its various embodiments discussed in this document. The generic normal proximal femur model 420 can be derived from statistical shape data constructed from multiple CT scans of normal proximal femurs of comparable anatomical origin from a group of subjects. The pathological proximal femur image 410 represents a CT scan of the proximal femur taken from a patient with femoroacetabular impingement (FAI). The normal proximal femur statistical shape (SS) model 420 can be registered onto the pathological impinged proximal femur image 410. Both the SS model 420 and the impinged proximal femur image 410 can be partitioned and labeled. A segment of the impinged proximal femur image 410 free of abnormity, such as the femur head 411, can be identified and matched to the corresponding femur head 421 of the SS model 420. The remaining segments of the impinged proximal femur image 410 can then be aligned to the respective remaining segments of the SS model 420. A comparison of the segments from the SS model 420 and the impinged proximal femur image 410 reveals a deformity region on the femur neck 412 of the impinged proximal femur image 410. The excess bone on the detected deformity region 412 can be defined as the volumetric difference between the detected deformity region 412 and the corresponding femur neck segment 422 on the SS model 420. The volumetric difference, as part of the surgical plan, defines the shape and volume on the pathological femur 410 that needs to be surgically removed.

Figure 4C:
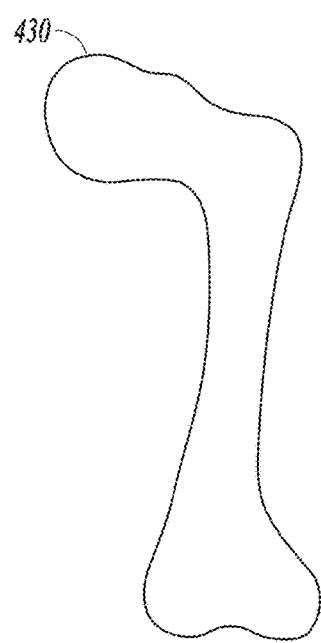
Figure 4D:
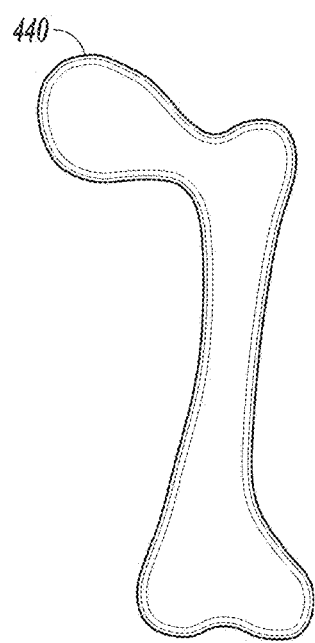
Figure 4E:
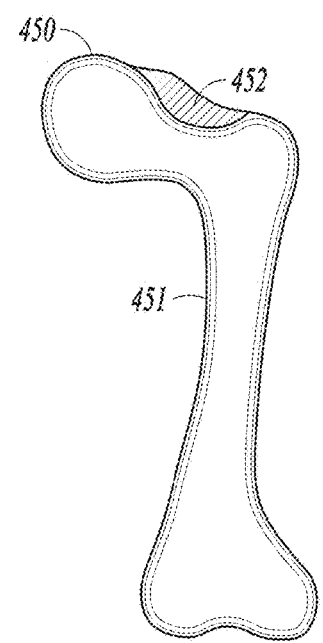

FIGS. 4C-E illustrates an example of a two-dimensional (2D) pathological femur representation 430 (as shown in FIG. 4C) with deformed region detected using a 2D generic normal femur model 440 (as shown in FIG. 4D). The generic normal femur model 440 can be generated and presented using the system 100 or its various embodiments discussed in this document. The generic normal femur model 440 can be a statistical model, a geometric model, or a parametric model constructed from multiple images of normal femurs of comparable anatomical origin. Following the registration of the generic normal femur model 440 to the pathological femur representation 430, a registered femur model 450 can be generated (as shown in FIG. 4E). By matching the registered femur model 450 to the pathological femur representation 430, an abnormity-free region 451 (which can include one or more abnormity-free segments) can be identified. By aligning the remaining segments of the registered femur model 450 to the corresponding segments of the pathological femur representation 430, a deformity region 452 can be detected. The deformity region 452, as illustrated in FIG. 4E, defines the shape of the excess bone tissues on the pathological femur representation 430 that can be surgically removed. The 2D example illustrated in FIGS. 4C-E is provided primarily to illustrate the concepts of segmentation and fitting a generic model to a pathological model. The method of segmentation and correlation illustrated by the 2D example are directly applicable to 3D models discussed above in reference to FIGS. 4A-B.

Figure 5:
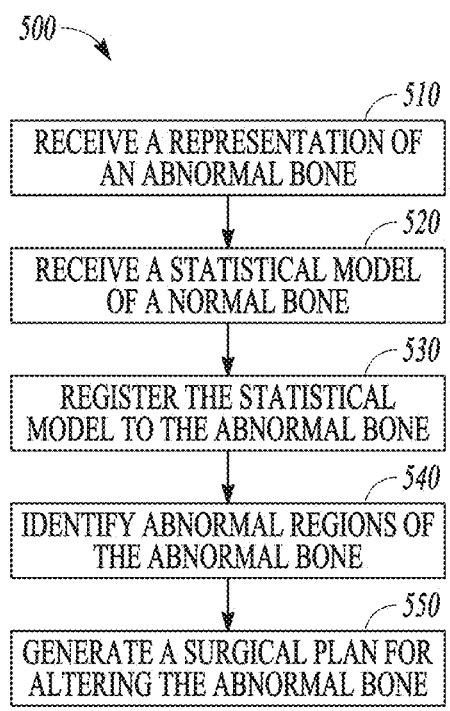
FIG. 5 is a flowchart that illustrates an example of a method for planning a surgery on an abnormal bone.

FIG. 5 is a flowchart that illustrates an example of a method for planning a surgery on an abnormal bone. In an embodiment, the system 100, including its various embodiments discussed in this document, is programmed to perform method 500, including its various embodiments discussed in this document.

A representation of an abnormal bone or a portion of the abnormal bone is received at 510. The abnormal bone can be a pathological bone undergoing surgical planning for alteration, repair, or removal. The abnormal bone representation can include a data set characterizing the abnormal bone. In an example, the data set includes geometric characteristics including location, shape, contour, or appearance of the anatomical structure. In another example, the data set can include intensity information. In various examples, the abnormal bone representation can include at least one medical image such as an X-ray, an ultrasound image, a computed tomography (CT) scan, a magnetic resonance (MR) image, a positron emission tomography (PET) image, a single-photon emission computed tomography (SPECT) image, or an arthrogram, among other 2D or 3D images. The abnormal bone representation can also include one or more point clouds. In some examples, the abnormal bone representation can be received from a database storing the data set characterizing the abnormal bone, or from an imaging system or an image acquisition module including an X-ray machine, a CT scanner, an MRI machine, a PET scanner, among others.

At 520, a generic normal bone model can be received. The generic normal bone model includes a data set representing a normal bone or a portion of the normal bone having an anatomical origin comparable to the abnormal bone received at 510. The generic normal bone model can represent the shape or appearance of the anatomical structure of the normal bone. The generic normal bone model may be in one of the forms including a parametric model, a statistical model, a shape-based model, a volumetric model, or other geometric models. The generic normal bone model can also be based on physical properties of the normal bone, including, for example, an elastic model, a spline model, or a finite element model. In some examples, the generic normal bone model can represent a desired postoperative shape or appearance of the normal bone. The desired postoperative shape or appearance of the normal bone can be obtained by modifying a normal bone model (such as a parametric model, a statistical model, a shape-based model, or a volumetric model) using a computer software configured for three-dimensional manipulation of the normal bone model.

In various examples, the generic normal bone model may include a statistical model created from a plurality of images or point clouds from normal bones of comparable anatomical origin from a group of subjects. The data used for generating the generic normal bone model may include shape data or appearance data. The shape data may include geometric features such as landmarks, surfaces, or boundaries; whilst the appearance data may include both geometric features and intensity information. In one example, the generic normal bone model includes a statistical shape (SS) model. The SS model can be derived from a plurality of medical images taken from normal bones of comparable anatomical origin from a group of subjects known to have normal bone anatomy. Examples of the medical images include an X-ray, an ultrasound image, a CT scan, an MR image, a PET image, a SPECT image, or an arthrogram, among other 2D and 3D images. In various embodiments, the shape data or appearance data can be constructed from medical images or the point clouds of normal bones of comparable anatomical origin from a group of subjects with similar age, gender, ethnicity, size, or other physical or demographical data. In some embodiments, the generic normal bone model has a comparable data format or modality as the abnormal bone representation. For example, if a CT scan of the pathological proximal femur from a patient is received at 510, then the SS model received at 520 can be constructed from the CT scans of proximal femurs with normal anatomy from a plurality of subjects. In another example, a CT scan of the pathological acetabulum from a patient can be received at 510, and the SS model received at 520 can be constructed from the CT scans of normal acetabula with normal anatomy from a plurality of subjects.

At 530, the generic normal bone model can be registered to the abnormal bone representation. The generic normal bone model and the abnormal bone representation can each be partitioned into a plurality of segments representing various anatomical structures on the respective image. The segments can be labeled such that the segments with the same label share specified characteristics such as a shape, anatomical structure, or intensity. In partitioning the abnormal bone representation, the pathological portion can be differentiated from the normal portion of the abnormal bone representation, and a registration area free of anatomical abnormality can be identified from the abnormal bone representation.

To register the generic normal bone model to the abnormal bone representation, the generic normal bone model can be transformed to create a registered generic model. The transformation can include a rigid transformation that brings the generic normal bone model in global alignment with the size and orientation of the abnormal bone representation. Examples of the rigid transformation include translation, rotation, or reflection. The transformation can also include a non-rigid transformation to reduce the local geometric discrepancies by aligning the generic normal bone model with the abnormal bone representation. Examples of non-rigid transformation include stretching, shrinking, or model-based transformations including radial basis functions, splines, or finite element models. In an example, both a rigid and non-rigid transformations can be applied to the generic normal bone model.

In some embodiments, a desired transformation $\Theta_{opt}$ can be determined as the one that minimizes the difference between the identified abnormity-free segments on the abnormal bone representation $S_{abnormal}(x,y,z)$ and the corresponding segments of the generic normal bone model $S_{model}(x,y,z)$ generic normal bone model following the transformation $\Theta$. That is, the desired transformation $\Theta_{opt}$ is selected such that the Euclidian distance $\|\Theta(S_{model}(x,y,z)) - S_{abnormal}(x,y,z)\|$ is minimized. The desired transformation can then be applied to the generic normal bone model to create the registered generic model. Then, in response to identifying the registration area of the abnormal bone, one or more segments of the registered generic model can be matched to the corresponding registration area of the abnormal bone. The remaining segments of the registered generic model can be aligned with the remaining segments of the abnormal bone representation based at least in part on the matching.

At 540, one or more abnormal regions of the abnormal bone can be detected. The abnormity can be detected using a comparison between the registered generic model and the abnormal bone representation. In an example, a plurality of model features can be extracted from the registered generic model, and a plurality of abnormal bone features can be extracted from the abnormal bone representation. Examples of the extracted features include one or more geometric parameters such as a location, an orientation, a curvature, a contour, a shape, an area, a volume, or other geometric parameters. The extracted features can also include one or more intensity-based parameters.

A degree of disconformity between a segment of the registered generic model and the matched segment of the abnormal bone representation can be calculated. For example, if a similarity measures between the abnormal bone feature of the segment ($R_{abnormal}(k)$) and the model feature of the corresponding segment on the registered generic model ($R_{model}(k)$) meets a specified criterion, the segment of the abnormal bone is declared to be abnormal. Examples of the similarity measures include distance in a normed vector space (such as L1 norm, L2 norm or Euclidian distance, and infinite norm), correlation coefficient, mutual information, or ratio image uniformity, among others. In an embodiment, the similarity measure can be determined according to the type of the feature or the modality of the image. For example, when geometric features are extracted from a 3D image of the abnormal bone and from an SS model which is derived from 3D medical images of the comparable bone anatomy, a volumetric difference, such as the sum of squared distance in the 3D normed vector space can be computed between the model features and the abnormal bone features.

In some embodiments, statistical distribution of a model feature can be used in calculating the degree of disconformity. For example, the generic normal bone model can be derived from images of bones of comparable anatomical origin from M subjects (M≥2). In determining the statistical distance between an N-dimensional abnormal bone feature vector Y=[y(1), y(2), . . . , y(N)] and an N-dimensional model feature vector X=[x(1), x(2), . . . , x(N)], the feature data from M subjects $X_m$=[$x_m$(1), $x_m$(2), . . . , $x_m$(N)] (m=1, 2, . . . , M) can be used to estimate a covariance matrix $C_{xx}$ of the model feature vector X as shown in equation (1):

$$C_{xx} = \frac{1}{M-1} \sum_{m=1}^{M} (X_m - X) \cdot (X_{nm} - X)^T \quad (1)$$

The statistical distance between the abnormal bone feature vector Y and model feature vector X can then be computed as the Mahalanobis distance as given in (2):

$$D_{XY} = \sqrt{(Y-X)^T C_{XX}^{-1} (Y-X)} \quad (2)$$

At 550, a surgical plan is generated. The surgical plan can define the location, shape, and volume of the portion of the abnormal bone from the one or more abnormal regions that need to be altered. In one example, for a segment with detected abnormal region, a volumetric parameter $X_{abnormal}(k)$ represents a shape or a volume of a segment of the abnormal bone representation, and a volumetric parameter $X_{model}(k)$ represents a shape or a volume of the corresponding segment of the registered generic model. The volumetric parameter $X_{model}(k)$ can then be subtracted from the volumetric parameter $X_{abnormal}(k)$, and the resulting subtracted volumetric parameter can be determined as the part of alteration. In an example, the surgical plan can include instructions for performing a first simulation of the abnormal bone and a second simulation of the surgically altered abnormal bone, such as a simulated model of the post-operative abnormal bone with the identified excess bone tissue removed. One or both of the first and the second simulations can each include a biomechanical simulation for evaluating one or more biomechanical parameters including, for example, range of motion of the respective bone. One or more abnormal regions of the abnormal bone can be detected using a comparison between the first simulation and the second simulation. In some embodiments, a graphical representation can be generated to illustrate one or more of the generic normal bone model, the abnormal bone representations, and the surgical plan. The graphical representation provides feedback to enable a system user to accept or modify the surgical plan. In some examples, the surgical plan can include instructions for incrementally altering the one or more abnormal regions of the abnormal bone by gradually removing the identified excess bone tissue from the abnormal bone such as following a pre-specified procedure.

Figure 6:
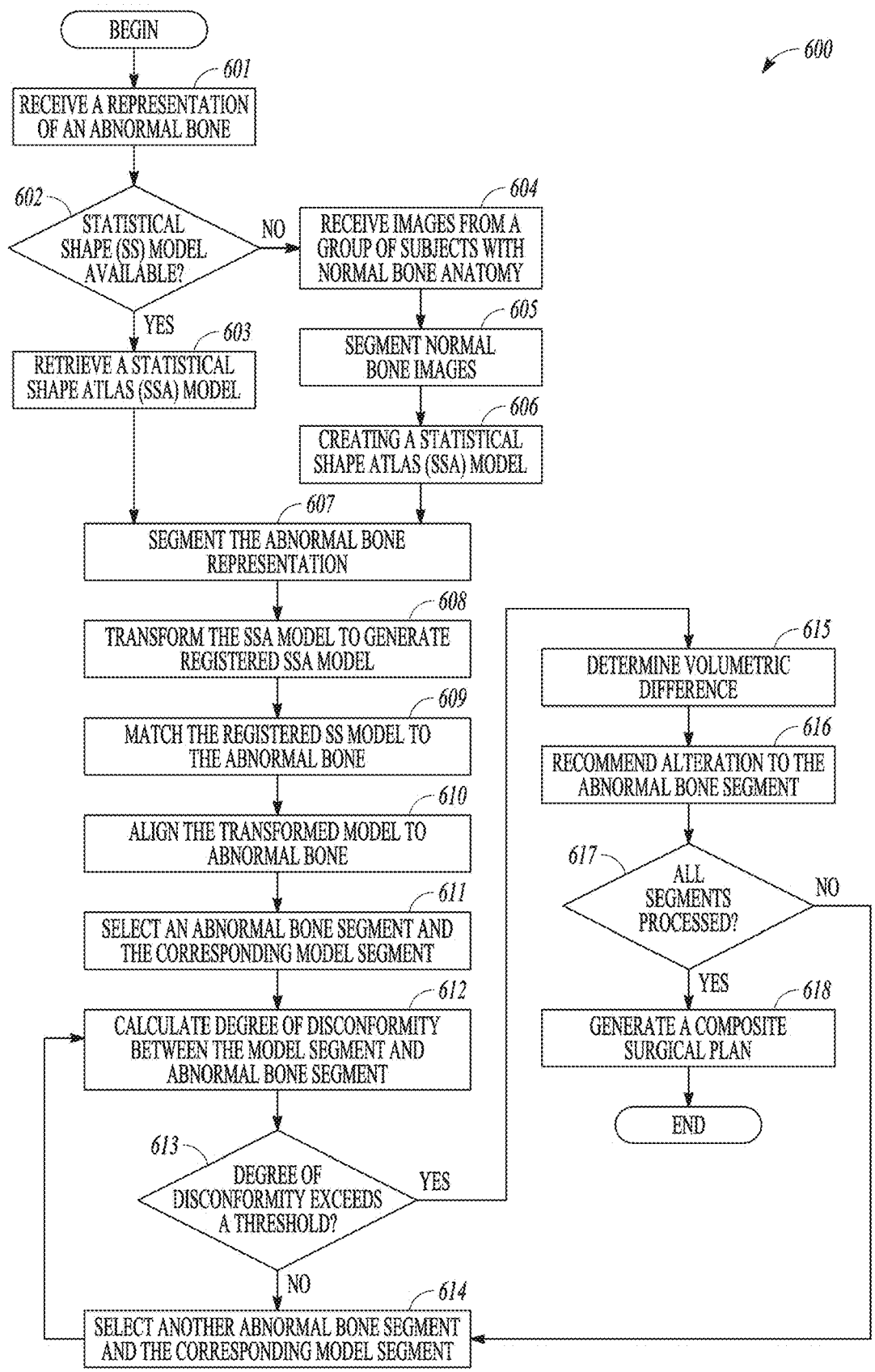
FIG. 6 is a flowchart that illustrates an example of a method for planning a surgical alteration of a portion of a diseased femur.

FIG. 6 is a flowchart that illustrates an example of a method 600 for planning a surgical alteration of a portion of a diseased bone such as a diseased femur, a diseased acetabulum, or other diseased bone in the body. One example of the alteration surgery is the treatment of femoroacetabular impingement (FAI). Surgical treatment of FAI includes removal of the excess bone from the femoral neck using, for example, a high speed bur or an arthroscopic shaver. The method 600 can be used to identify the abnormal regions of impingement and generate a surgical plan including the shape and volume of bone removal, thereby providing instructions to guide a surgical tool in the surgery. In an embodiment, the system 100, including its various embodiments discussed in this document, is programmed to perform method 600, including its various embodiments discussed in this document.

A representation of the abnormal bone is received at 601. The representation can include a data set characterizing the abnormal bone. In an example, the representation can be one or more medical images of the diseased femur, such as an X-ray, an ultrasound image, a CT scan, an MR image, a PET image, a SPECT image, or an arthrogram, among other 2D and 3D images. In another example, the representation can include one or more point clouds of the diseased femur.

At 602, the availability of a generic normal model is checked. The generic normal bone model can include a data set representing a normal bone which has an anatomical origin comparable to the abnormal bone in question. One example of the generic model includes a statistical shape (SS) model of a normal femur. The normal femur SS model can be derived from statistical shape data constructed from multiple medical images of normal femurs from comparable anatomical origin from a group of subjects. The generic normal bone model can have a comparable data format or image modality as the abnormal bone representation received at 601. For example, if a CT scan image of the pathological femur is received at 601, then at 602 an statistical shape (SS) model derived from CT scans of normal femurs of comparable anatomical origin can be searched for subsequent use.

If the generic normal bone model is available (e.g., found in a SS model database) at 602, then at 603 the generic normal bone model can be retrieved for further use. If the model is not available, then a generic normal bone model can be created. As illustrated in FIG. 6, at 604, a plurality of images of normal bones with anatomical origin comparable to the received abnormal bone can be retrieved from an image database or other storage devices. In an example, the images can have a comparable data format or image modality as the received abnormal bone representation, and can be taken from a group of subjects having similar physical or demographical data as the host (patient) of the abnormal bone under analysis. In some examples, even if the SS model is available at 602, it may be desirable to recreate an SS model using data of normal bones from a specified group of subjects such as having demographic data comparable to the host of the abnormal bone.

The images thus received at 604 comprise statistical shape data. The statistical shape data can then be partitioned into a plurality of segments at 605. Each image in the statistical shape data can be partitioned according to various anatomical structures of the normal bone. For example, an image of the proximal femur can be partitioned into image segments of femur head, femur neck, fovea of head, greater trochanter, and lesser trochanter, among others. The partitioned segments each may be assigned a label such that the segments with the same label share specified characteristics such as a shape, anatomical structure, or intensity.

The partitioned statistical shape data can then be used to create an SS model at 606. In some examples, the SS model can be created by computing statistical distributions of shapes and/or intensities of the segments from the shape data or appearance data. Other methods, such as a principal component analysis, regression analysis, and parametric modeling can be used to create the SS model.

At 607, the abnormal bone can be partitioned into different segments. The SS model can also be partitioned if no segments are available (for example, the SS model directly retrieved from a database at 603). In an example, the partition of the abnormal bone can be performed using a similar method as partitioning the images in statistical shape data. As a result, correspondence can be established between the segments of the SS model and the segments of the abnormal bone representation. From the partitioned segments of the abnormal bone, a registration area free of anatomical abnormity can be identified.

The SS model can be transformed at 608 to generate a registered SS model. The registered SS model can be in a coordinate system similar to that of the abnormal bone representation. Examples of the transformation can include scaling, rotation, translation, expansion, dilation, or other affine transformation. Then, in response to identifying the registration area of the abnormal bone free of anatomical abnormity, one or more segments of the registered SS model can be matched to the corresponding registration area of the abnormal bone at 609. The remaining segments of the registered SS model can then be aligned with the remaining segments of the abnormal bone representation at 610, based at least in part on the matching results from 609.

An abnormal bone segment can then be selected and compared to the corresponding segment of the registered SS model at 611. In an embodiment, a pool of abnormal bone segments suspected of deformity can be pre-selected such as by the surgeon, and each of the suspected segments of deformity can be compared to the corresponding segment of the registered SS model. A degree of disconformity between the abnormal bone segment and the corresponding registered SS model segment can be computed at 612. The degree of disconformity can be calculated, for example, as a statistical distance between one or more features extracted from the abnormal bone segment and the one or more features extracted from the corresponding SS model segment. Examples of the extracted features include volumetric parameters such as area, shape, or volume. Examples of the statistical distance include L1 norm, L2 norm (i.e., Euclidian distance), infinite norm or other norms in the normed vector space, correlation coefficient, or mutual information, among others.

The degree of disconformity can then be compared to a specified criterion such as a threshold at 613. If the degree of disconformity falls below the threshold, then no deformity is detected in the present abnormal bone segment. A different abnormal bone segment can be selected at 614 such as from the pool of suspected segments of deformity. The corresponding segment of the registered SS model can also be selected and the degree of disconformity can be calculated for the suspected segment at 612. If at 613 the degree of disconformity meets the specified criterion (e.g., exceeds the threshold), then deformity is detected for the present abnormal bone segment; and a volumetric difference between the abnormal bone segment and the corresponding segment of the registered SS model can be calculated at 615. In an example, the volumetric parameters of the segment of the registered SS model can be subtracted from the corresponding volumetric parameters of the abnormal bone segment. A surgical plan is generated at 616 including recommending an alteration, repair, or removal of the subtracted volumes on the abnormal bone. The surgical plan can also include comparison of a first simulation of the diseased femur and a second simulation of a model of surgically altered diseased femur. The simulation can be used for evaluating one or more biomechanical parameters including, for example, range of motion of the respective bone.

The pool of suspected segments of deformity is then checked at 617. If there remain suspected segments of deformity, an abnormal bone segment can be selected from the pool at 614 and the disconformity calculation resumes at 612. If all suspected segments of deformity have been processed, then at 618 a composite surgical plan can be generated. In an example, the composite surgical plan comprises the recommended alterations to all the abnormal bone segments.

Figure 7:
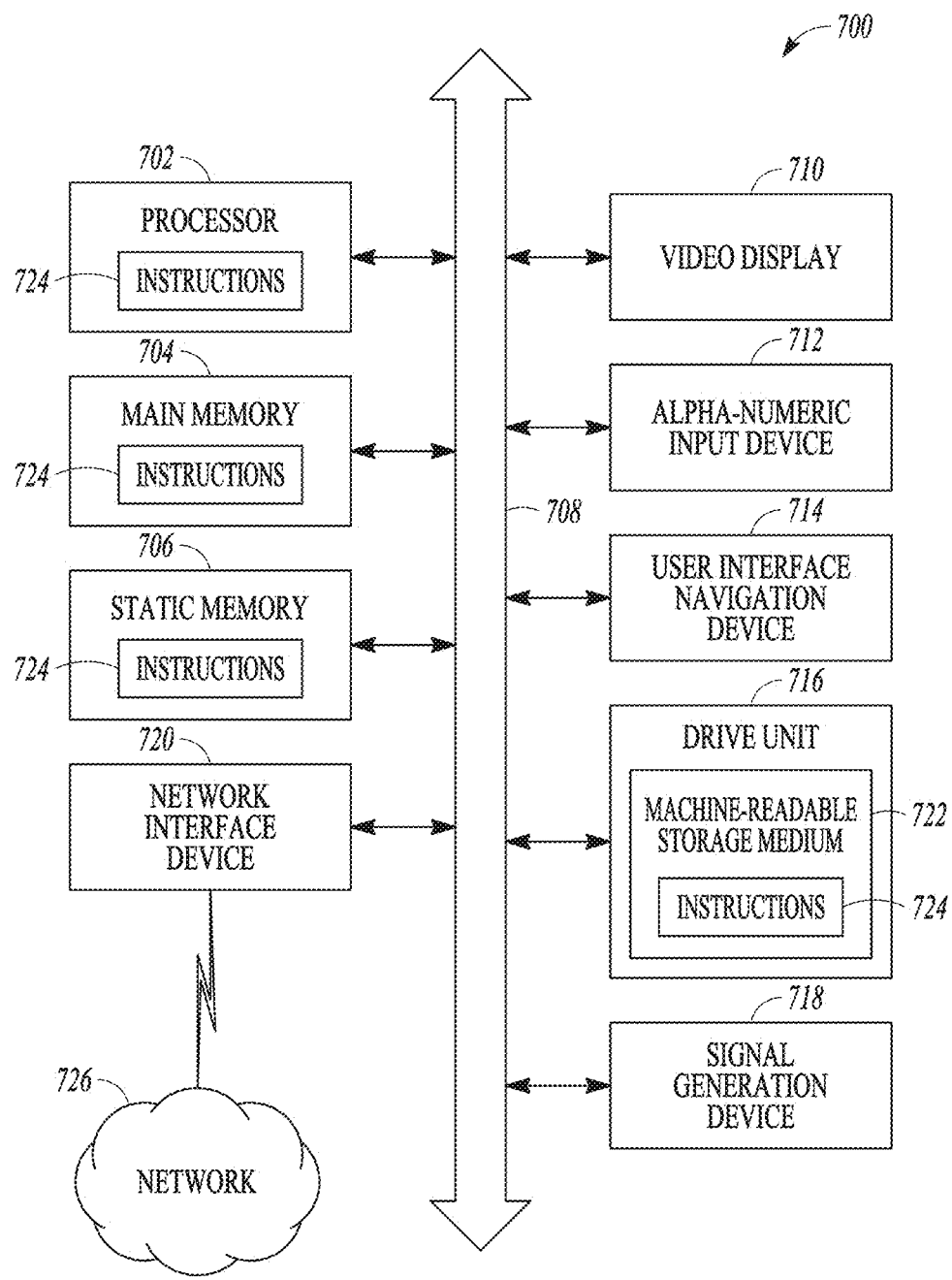
FIG. 7 is a block diagram that illustrates an example of a computer system within which instructions for causing the computer system to perform surgery planning may be executed.

FIG. 7 is a block diagram that illustrates an example of a machine in the form of a computer system 700 within which instructions, for causing the computer system to perform any one or more of the methods discussed herein, may be executed. In various embodiments, the machine can operate as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a PDA, a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 700 includes a processor 702 (such as a central processing unit (CPU), a graphics processing unit (GPU), or both), a main memory 704 and a static memory 706, which communicate with each other via a bus 708. The computer system 700 may further include a video display unit 710 (such as a liquid crystal display (LCD) or a cathode ray tube (CRT)), an alpha-numeric input device 712 (such as a keyboard), a user interface (UI) navigation device (or cursor control device) 714 (such as a mouse), a disk drive unit 716, a signal generation device 718 (e.g., a speaker) and a network interface device 720.

The disk drive unit 716 includes a machine-readable storage medium 722 on which is stored one or more sets of instructions and data structures (e.g., software) 724 embodying or used by any one or more of the methods or functions described herein. The instructions 724 may also reside, completely or at least partially, within the main memory 704, static memory 706, and/or within the processor 702 during execution thereof by the computer system 700, the main memory 704 and the processor 702 also constituting machine-readable media. In an example, the instructions 724 stored in the machine-readable storage medium 722 include instructions causing the computer system 700 to receive an abnormal bone representation including a data set representing the abnormal bone, to receive a generic normal bone model including a data set representing a normal bone having an anatomical origin comparable to the abnormal bone, to register the generic normal bone model to the abnormal bone representation to create a registered generic model, to identify one or more abnormal regions of the abnormal bone using a comparison between the registered generic model and the abnormal bone representation, and to generate a surgical plan for altering a portion of the abnormal bone from the one or more abnormal regions.

To direct the computer system 700 to generate the surgical plan, the machine-readable storage medium 722 may further store the instructions 724 that cause the computer system 700 to generate data representing one or more of a volume, a shape, a location, or an orientation of the one or more abnormal regions in reference to the generic normal bone model, and to guide a surgical a surgical tool or surgical system (such as a surgical navigation and/or medical robotics) in altering the portion of the abnormal bone. The instructions in the machine-readable storage medium 722 may also cause the computer system 700 to generate a graphical representation illustrating one or more of the generic normal bone model, the abnormal bone representations, and the surgical plan, and to receive command from a system user to modify the surgical plan.

While the machine-readable medium 722 is shown in an example embodiment to be a single medium, the term "machine-readable medium" may include a single medium or multiple media (e.g., a centralized or distributed database, and/or associated caches and servers) that store the one or more instructions or data structures. The term "machine-readable storage medium" shall also be taken to include any tangible medium that is capable of storing, encoding or carrying instructions for execution by the machine and that cause the machine to perform any one or more of the methods of the present invention, or that is capable of storing, encoding or carrying data structures used by or associated with such instructions. The term "machine-readable storage medium" shall accordingly be taken to include, but not be limited to, solid-state memories, and optical and magnetic media. Specific examples of machine-readable media include non-volatile memory, including by way of example, semiconductor memory devices (e.g., erasable programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks. A "machine-readable storage medium" shall also include devices that may be interpreted as transitory, such as register memory, processor cache, and RAM, among others. The definitions provided herein of machine-readable medium and machine-readable storage medium are applicable even if the machine-readable medium is further characterized as being "non-transitory." For example, any addition of "non-transitory," such as non-transitory machine-readable storage medium, is intended to continue to encompass register memory, processor cache and RAM, among other memory devices.

In various examples, the instructions 724 may further be transmitted or received over a communications network 726 using a transmission medium. The instructions 724 may be transmitted using the network interface device 720 and any one of a number of well-known transfer protocols (e.g., HTTP). Examples of communication networks include a LAN, a WAN, the Internet, mobile telephone networks, plain old telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method for facilitating automated control of a robotic surgical tool for improving a surgical procedure on an abnormal bone, comprising:

partitioning, by a computing device, a representation of the abnormal bone and a generic normal bone model into first and second pluralities of segments, respectively, wherein the generic normal bone model is generated from a plurality of sets of image data for normal bones having an anatomical origin comparable to the abnormal bone from a group of subjects having normal bone anatomy;

matching, by the computing device, one or more segments of the first plurality of segments partitioned from the representation of the abnormal bone comprising a registration area free of anatomical abnormality to one or more segments of the second plurality of segments partitioned from the generic normal bone model;

aligning, by the computing device, each of one or more remaining segments of the second plurality of segments partitioned from the generic normal bone model with a corresponding one of one or more remaining segments of the first plurality of segments partitioned from the representation of the abnormal bone based on the matching;

calculating, by the computing device, a degree of disconformity based on a difference between a first volume of an aligned one of the one or more remaining segments of the second plurality of segments partitioned from the generic normal bone model and a second volume of the corresponding one of the one or more remaining segments of the first plurality of segments partitioned from the representation of the abnormal bone, wherein the aligned one of the one or more remaining segments of the second plurality of segments partitioned from the generic normal bone model has an anatomical region comparable to the corresponding one of the one or more remaining segments of the first plurality of segments partitioned from the representation of the abnormal bone, wherein the difference comprises a volumetric difference in a normed vector space;

determining, by the computing device, whether the calculated degree of disconformity exceeds a threshold indicating that the corresponding one of the one or more remaining segments of the first plurality of segments partitioned from the representation of the abnormal bone comprises one or more abnormal regions;

generating, by the computing device, a surgical plan for altering a portion of the abnormal bone within the one or more abnormal regions when the determination indicates that the calculated degree of disconformity exceeds the threshold;

generating, by the computing device, a graphical representation illustrating one or more of the generic normal bone model, the representation of the abnormal bone, or the surgical plan, the graphical representation providing feedback to enable a system user to accept or modify the surgical plan; and guiding, by the computing device, a robotic surgical tool to perform one or more operations to alter the portion of the abnormal bone based on the surgical plan.

2. The method of claim 1, further comprising:
transforming, by the computing device, the generic normal bone model to register the generic normal bone model in a substantially similar coordinate system as that of the representation of the abnormal bone.

3. The method of claim 1, wherein calculating, by the computing device, the degree of disconformity further comprises:
extracting, by the computing device, a plurality of model features from the aligned one of the one or more remaining segments of the second plurality of segments partitioned from the generic normal bone model and a plurality of abnormal bone features from the corresponding one of the one or more remaining segments of the first plurality of segments partitioned from the representation of the abnormal bone;
calculating, by the computing device, a statistical distribution of the second plurality of model features using data of the normal bones from which the generic normal bone model is derived; and
calculating, by the computing device, a statistical distance between the second plurality of model features and the second plurality of abnormal bone features using the statistical distribution.

4. The method of claim 1, wherein generating, by the computing device, the surgical plan further comprises:
subtracting, by the computing device, for each of the one or more abnormal regions, the first volume from the second volume; and
determining, by the computing device, a part of the alteration based on the subtraction.

5. The method of claim 1, further comprising generating, by the computing device, the generic normal bone model based on a parametric model comprising one or more parameters characterizing the normal bone anatomy.

6. The method of claim 1, further comprising identifying, by the computing device, various anatomical structures of a normal bone in the plurality of sets of image data, and results in a partitioned statistical shape data set comprising images of the normal bones partitioned according to the anatomical structures.

7. The method of claim 6, further comprising generating, by the computing device, a statistical shape (SS) model based on, and subsequent to generating, the partitioned statistical shape data set, wherein the SS model comprises a statistical representation of the normal bone anatomy from the group of subjects.

8. A surgical computing device, comprising:
a non-transitory computer readable medium comprising programmed instructions stored thereon for facilitating automated control of a robotic surgical tool for improving a surgical procedure on an abnormal bone; and
one or more processors coupled to the non-transitory computer readable medium and configured to execute the stored programmed instructions to:
partition a representation of the abnormal bone and a generic normal bone model into first and second pluralities of segments, respectively, wherein the generic normal bone model is generated from a plurality of sets of image data for normal bones having an anatomical origin comparable to the abnormal bone from a group of subjects having normal bone anatomy;
match one or more segments of the first plurality of segments partitioned from the representation of the abnormal bone comprising a registration area free of anatomical abnormality to one or more segments of the second plurality of segments partitioned from the generic normal bone model;
align each of one or more remaining segments of the second plurality of segments partitioned from the generic normal bone model with a corresponding one of one or more remaining segments of the first plurality of segments partitioned from the representation of the abnormal bone based on the matching;
calculate a degree of disconformity based on a difference between a first volume of an aligned one of the one or more remaining segments of the second plurality of segments partitioned from the generic normal bone model and a second volume of the corresponding one of the one or more remaining segments of the first plurality of segments partitioned from the representation of the abnormal bone, wherein the aligned one of the one or more remaining segments of the second plurality of segments partitioned from the generic normal bone model has an anatomical region comparable to the corresponding one of the one or more remaining segments of the first plurality of segments partitioned from the representation of the abnormal bone, wherein the difference comprises a volumetric difference in a normed vector space;
determine whether the calculated degree of disconformity exceeds a threshold indicating that the corresponding one of the one or more remaining segments of the first plurality of segments partitioned from the representation of the abnormal bone comprises one or more abnormal regions;

generate a surgical plan for altering a portion of the abnormal bone within the one or more abnormal regions when the determination indicates that the calculated degree of disconformity exceeds the threshold;

generate a graphical representation illustrating one or more of the generic normal bone model, the representation of the abnormal bone, or the surgical plan, the graphical representation providing feedback to enable a system user to accept or modify the surgical plan; and guide a robotic surgical tool to perform one or more operations to alter the portion of the abnormal bone based on the surgical plan.

9. The surgical computing device of claim 8, wherein the one or more processors are further configured to execute the stored programmed instructions to transform the generic normal bone model to register the generic normal bone model in a substantially similar coordinate system as that of the representation of the abnormal bone.

10. The surgical computing device of claim 8, wherein the one or more processors are further configured to execute the stored programmed instructions to:

extract a plurality of model features from the aligned one of the one or more remaining segments of the second plurality of segments partitioned from the generic normal bone model and a plurality of abnormal bone features from the corresponding one of the one or more remaining segments of the first plurality of segments partitioned from the representation of the abnormal bone;

calculate a statistical distribution of the second plurality of model features using data of the normal bones from which the generic normal bone model is derived; and calculate a statistical distance between the second plurality of model features and the second plurality of abnormal bone features using the statistical distribution.

11. The surgical computing device of claim 8, wherein the one or more processors are further configured to execute the stored programmed instructions to:

subtract, for each of the one or more abnormal regions, the first volume from the second volume; and determine a part of the alteration based on the subtraction.

12. The surgical computing device of claim 8, wherein the one or more processors are further configured to execute the stored programmed instructions to generate the generic normal bone model based on a parametric model comprising one or more parameters characterizing the normal bone anatomy.

13. The surgical computing device of claim 8, wherein the one or more processors are further configured to execute the stored programmed instructions to identify various anatomical structures of a normal bone in the plurality of sets of image data, and results in a partitioned statistical shape data set comprising images of the normal bones partitioned according to the anatomical structures.

14. The surgical computing device of claim 13, wherein the one or more processors are further configured to execute the stored programmed instructions to generate a statistical shape (SS) model based on, and subsequent to generating, the partitioned statistical shape data set, wherein the SS model comprises a statistical representation of the normal bone anatomy from the group of subjects.

15. A non-transitory computer readable medium having stored thereon instructions for facilitating automated control of a robotic surgical tool for improving a surgical procedure on an abnormal bone, comprising executable code that, when executed by one or more processors, causes the one or more processors to:

partition a representation of the abnormal bone and a generic normal bone model into first and second pluralities of segments, respectively, wherein the generic normal bone model is generated from a plurality of sets of image data for normal bones having an anatomical origin comparable to the abnormal bone from a group of subjects having normal bone anatomy;

match one or more segments of the first plurality of segments partitioned from the representation of the abnormal bone comprising a registration area free of anatomical abnormality to one or more segments of the second plurality of segments partitioned from the generic normal bone model;

align each of one or more remaining segments of the second plurality of segments partitioned from the generic normal bone model with a corresponding one of one or more remaining segments of the first plurality of segments partitioned from the representation of the abnormal bone based on the matching;

calculate a degree of disconformity based on a difference between a first volume of an aligned one of the one or more remaining segments of the second plurality of segments partitioned from the generic normal bone model and a second volume of the corresponding one of the one or more remaining segments of the first plurality of segments partitioned from the representation of the abnormal bone, wherein the aligned one of the one or more remaining segments of the second plurality of segments partitioned from the generic normal bone model has an anatomical region comparable to the corresponding one of the one or more remaining segments of the first plurality of segments partitioned from the representation of the abnormal bone, wherein the difference comprises a volumetric difference in a normed vector space;

determine whether the calculated degree of disconformity exceeds a threshold indicating that the corresponding one of the one or more remaining segments of the first plurality of segments partitioned from the representation of the abnormal bone comprises one or more abnormal regions;

generate a surgical plan for altering a portion of the abnormal bone within the one or more abnormal regions, when the determination indicates that the calculated degree of disconformity exceeds the threshold;

generate a graphical representation illustrating one or more of the generic normal bone model, the representation of the abnormal bone, or the surgical plan, the graphical representation providing feedback to enable a system user to accept or modify the surgical plan; and guide a robotic surgical tool to perform one or more operations to alter the portion of the abnormal bone based on the surgical plan.

16. The non-transitory computer readable medium of claim 15, wherein the executable code, when executed by the one or more processors, further causes the one or more processors to transform the generic normal bone model to register the generic normal bone model in a substantially similar coordinate system as that of the representation of the abnormal bone.

17. The non-transitory computer readable medium of claim 15, wherein the executable code, when executed by the one or more processors, further causes the one or more processors to:
  extract a plurality of model features from the aligned one of the one or more remaining segments of the second plurality of segments partitioned from the generic normal bone model and a plurality of abnormal bone features from the corresponding one of the one or more remaining segments of the first plurality of segments partitioned from the representation of the abnormal bone;
  calculate a statistical distribution of the second plurality of model features using data of the normal bones from which the generic normal bone model is derived; and
  calculate a statistical distance between the second plurality of model features and the second plurality of abnormal bone features using the statistical distribution.

18. The non-transitory computer readable medium of claim 15, wherein the executable code, when executed by the one or more processors, further causes the one or more processors to:
  subtract, for each of the one or more abnormal regions, the first volume from the second volume; and
  determine a part of the alteration based on the subtraction.

19. The non-transitory computer readable medium of claim 15, wherein the executable code, when executed by the one or more processors, further causes the one or more processors to generate the generic normal bone model based on a parametric model comprising one or more parameters characterizing the normal bone anatomy.

20. The non-transitory computer readable medium of claim 15, wherein the executable code, when executed by the one or more processors, further causes the one or more processors to identify various anatomical structures of a normal bone in the plurality of sets of image data, and results in a partitioned statistical shape data set comprising images of the normal bones partitioned according to the anatomical structures.

21. The non-transitory computer readable medium of claim 20, wherein the executable code, when executed by the one or more processors, further causes the one or more processors to generate a statistical shape (SS) model based on, and subsequent to generating, the partitioned statistical shape data set, wherein the SS model comprises a statistical representation of the normal bone anatomy from the group of subjects.

* * * * *